United States Patent
Wang et al.

(10) Patent No.: US 12,275,737 B2
(45) Date of Patent: Apr. 15, 2025

(54) POLYMORPHS OF A KINASE INHIBITOR, PHARMACEUTICAL COMPOSITIONS CONTAINING SUCH A COMPOUND, PREPARATION METHODS, AND APPLICATIONS

(71) Applicants: Meryx, Inc., Chapel Hill, NC (US); The University of North Carolina at Chapel Hill, Chapel Hill, NC (US); Betta Pharmaceuticals Co., Ltd, Zhejiang (CN)

(72) Inventors: Xiaodong Wang, Chapel Hill, NC (US); Weihe Zhang, Vestavia, AL (US); Xiangyong Liu, Zhejiang (CN); Changlong Han, Zhejiang (CN); Zongquan Li, Zhejiang (CN)

(73) Assignee: Meryx, Inc., Chapel Hill, NC (US)

( * ) Notice: Subject to any disclaimer, the term of this patent is extended or adjusted under 35 U.S.C. 154(b) by 752 days.

(21) Appl. No.: 17/594,104

(22) PCT Filed: Apr. 1, 2020

(86) PCT No.: PCT/US2020/026167
§ 371 (c)(1),
(2) Date: Oct. 1, 2021

(87) PCT Pub. No.: WO2020/205967
PCT Pub. Date: Oct. 8, 2020

(65) Prior Publication Data
US 2022/0162214 A1    May 26, 2022

Related U.S. Application Data (60) Provisional application No. 62/828,055, filed on Apr. 2, 2019.

(51) Int. Cl.
| | |
|---|---|
| *C07D 487/04* | (2006.01) |
| *A61K 31/519* | (2006.01) |
| *A61K 45/06* | (2006.01) |
| *A61P 35/00* | (2006.01) |
| *A61P 35/02* | (2006.01) |

(52) U.S. Cl.
CPC .......... *C07D 487/04* (2013.01); *A61K 31/519* (2013.01); *A61K 45/06* (2013.01); *A61P 35/00* (2018.01); *A61P 35/02* (2018.01); *C07B 2200/13* (2013.01)

(58) Field of Classification Search
CPC .... C07D 487/04; A61K 31/519; A61K 45/06; A61P 35/00; A61P 35/02; C07B 2200/13
See application file for complete search history.

(56) References Cited

U.S. PATENT DOCUMENTS 9,795,606 B2 * 10/2017 Wang ................... A61P 35/02
2022/0162214 A1    5/2022 Wang et al.

FOREIGN PATENT DOCUMENTS

| CN | 103958510 A | 7/2014 | |
|---|---|---|---|
| EP | 3947389 A | 2/2022 | |
| WO | 2013052417 A1 | 4/2013 | |
| WO | 2015157128 A1 | 10/2015 | |
| WO | WO-2017062797 A1 * | 4/2017 | ........... A61K 31/519 |

(Continued)

OTHER PUBLICATIONS

Gura et al., Science, 1997, 278:1041-1042 (Year: 1997).*

(Continued)

*Primary Examiner* — Sean M Basquill
*Assistant Examiner* — Jonathan D Mahlum
(74) *Attorney, Agent, or Firm* — Katten Muchin Rosenman LLP (57) ABSTRACT

The invention relates to new crystal forms of compound (trans)-4-((2-cyclopropylethyl)amino)-5-(4-((4-methylpiperazin-1-yl)methyl)phenyl)-7H-pyrrolo[2,3-d]pyrimidin-7-yl) cyclohexanol trihydrochloride, its hydrate, or solvate, as shown in Formula I. The invention also relates to methods for preparation of the described compound, crystal form, and related intermediate compounds, as well as pharmaceutical compositions containing the compounds. Further described is, the use of the compounds or crystal forms in the production of a medicament for the treatment of a disease, symptom, or condition, or the use in treatment of a disease, symptom or condition.

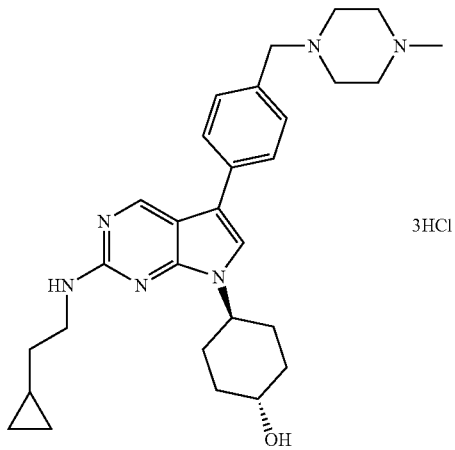

Formula I

16 Claims, 6 Drawing Sheets

(56) References Cited

FOREIGN PATENT DOCUMENTS

WO 2019006548 A1 1/2019

OTHER PUBLICATIONS

Johnson et al., Br J Cancer, 2001, 84:1424-1431 (Year: 2001).*
Kunnumakkara et al., Exp Biol Med, 2019; 244:663-689 (Year: 2019).*
Graham et al., Nat Rev Cancer, 2014, 14:769-785 (Year: 2014).*
Daver et al., Leukemia, 2019, 33:299-312 (Year: 2019).*
Tanim et al., Int J Mol Sci 2024, 25:7660 (Year: 2024).*
Boyle et al., Growing Crystals That Will Make Your Crystallographer Happy, retrieved from https://web.archive.org/web/20070304084151/http://www.xray.ncsu.edu/GrowXtal.html#expand on Aug. 12, 2024 (Year: 2007).*
Minson, K. A. et al. "The MERTK/FLT3 inhibitor MRX-2843 overcomes resistance-conferring FLT3 mutations in acute myeloid leukemia" JCI Insight, 2016, vol. 1, No. 3, Article e85630, internal pp. 1-16, internal p. 2; figure 1.
Examiner's report for CA Application No. 3,146,373, with a mailing date of Apr. 3, 2024.
Byrn, et al., "Pharmaceutical Solids: A Strategic Approach to Regulatory Considerations", Pharma. Res., 12/7, pp. 945-954, 1995.
Bavin, "Polymorphism in Process Development", Chemistry and Industry, pp. 527-529, Aug. 21, 1989 (Aug. 21, 1989).
Carlson, et al., "An integrated high throughput workflow for pre-formulations: Polymorph and salt selection studies", Pharm. Chem, Drug Development, pp. 10-15, 2003.
Zhang, Z.Y., "Functional studies of protein tyrosine phosphatases with chemical approaches," Biochim Biophys Acta, 2005, 1754(1-2):100-107.
Graham, D.K. et al., "Cloning and mRNA expression analysis of a novel human proto oncogene, c-mer," Cell Growth Differ., 1994, 5(6):647-657.
Ling, L. et al., "Identification of the major autophosphorylation sites of Nyk/Mer, an NCAM-related receptor tyrosine kinase," Biol. Chem., 1996, 271(31):18355-18362.
Linger, R.M., et al., "Mer receptor tyrosine kinase is a novel therapeutic target in pediatric B-cell acute lymphoblastic leukemia," Blood, 2009, 114(13):2678-2687.
Lee-Sherick, A.B., et al., "Targeting pediatric acute lymphoblastic leukemia: novel therapies currently in development." Br. J. Haematol., 2010, 151(4):295-311.
Nguyen, K. et al., "Factors influencing survival after relapse from acute lymphoblastic leukemia: a children's oncology group study," Leukemia, 2008, 22(12):2142-2150.
Liao, J.J., "Molecular recognition of protein kinase binding pockets for design of potent and selective kinase inhibitor," J. Med. Chem., 2007, 50(3):409-424.
Hatzimichael, E. et al., "Profile of pacritinib and its potential in the treatment of hematologic disorder," J. Blood Med., 2014, 5:143-152.
Smith, C.C., et al., "Validation of ITD mutations in FLT3 as a therapeutic target in human an acute myeloid leukaemia," Nature, 2012, 485(7397):260-263.
The extended European search report dated Dec. 13, 2022, from European Patent Application No. 20783939.0, 7 sheets.
Zhang Weihe et al: "UNC2025, a Potent and Orally Bioavailable MER/FLT3 Dual Inhibitor", Journal of Medicinal Chemistry, vol. 57, No. 16, Aug. 6, 2014 (Aug. 6, 2014), pp. 7031-7041, XP093005047, US ISSN:0022-2623, DOI: 10.1021/jm500749d; & Zhang Weihe et al: "Supplemental Information—UNC2025, a potent and orally bioavailable Mer/Flt 3 dual inhibitor", Journal of Medicinal Chemistry, Aug. 28, 2014 (Aug. 28, 2014), pp. 1-17, XP093005052, [retrieved on Dec. 5, 2022].
Bipul Sarma et al: "Solid forms of pharmaceuticals: Polymorphs, salts and co-crystals", Korean J. Cherm. Eng., vol. 28, No. 2, Jan. 1, 2022 (Jan. 1, 2011), pp. 315-322, XP055402417, DOI: 10.1007/s11814-010-0520-0.
First Office Action issued Mar. 11, 2023, from Chinese Application No. 202080027507.X, 8 sheets.
First Examination Report for AU Application 2020256186, with a mailing date of Feb. 3, 2025.

* cited by examiner

POLYMORPHS OF A KINASE INHIBITOR, PHARMACEUTICAL COMPOSITIONS CONTAINING SUCH A COMPOUND, PREPARATION METHODS, AND APPLICATIONS

TECHNICAL FIELD

The currently disclosed subject matter falls into the field of pharmaceutical crystal forms, and specifically, it relates to polymorphs of a kinase inhibitor, pharmaceutical compositions containing such compounds, preparation methods, and applications thereof.

BACKGROUND

Protein tyrosine kinase (PTK) is a main family of enzymes that function to transfer a phosphate group to protein tyrosine residues, thus activating the phenolic hydroxyl groups. PTKs play an important role in the processes of cell proliferation and malignancy. PTKs include receptor PTKs (receptor tyrosine kinase, RTK) and non-receptor PTKs (see Zhang, Z. Y, "Functional studies of protein tyrosine phosphatases with chemical approaches," *Biochim Biophys Acta*, 2005, 1754(1-2):100-107).

The RTK family is a single-pass receptor that has endogenous PTK activity. Up to now, more than 50 RTKs belonging to 20 subfamilies have been identified, mainly including hepatocyte growth factor receptor, epidermal growth factor receptor, platelet-derived growth factor receptor, insulin and insulin-like growth factor-1 receptor, nerve growth factor receptor, fibroblast growth factor receptor, and vascular endothelial growth factor receptor. They play a key role in regulating signal transduction pathways relevant to cell proliferation, apoptosis, differentiation, and metabolism. The RTK family members consist of three components, including the extracellular portion that binds to the ligand, the transmembrane portion, and an intracellular portion having PTK activity and a downstream signal protein binding site.

Mer tyrosine kinase (Mer TK) belongs to the TAM (Axl/Tyro-3/Mer) RTK family. Mer genes of human beings were found by Graham in 1994 (see Graham, D. K. et al., "Cloning and mRNA expression analysis of a novel human proto-oncogene, c-mer," *Cell Growth Differ.*, 1994, 5(6): 647-657). The gene is located at 2q14.1 with total length of 130,755 kb and contains 19 exons, including 999 amino acids in coding, and a relative molecular mass of about 109,000. Mer protein consists of an extracellular domain, transmembrane domain, and intracellular kinase domain. The extracellular domain consists of two immunoglobulin domains and two fibronectin domains. The immunoglobulin domain is a combined domain of protein products encoded with growth arrest specific gene 6 (Gas6) while the fibronectin domain plays a regulatory role in combination of Mer and Gas 6. The intracellular kinase domain unique KWIAIES sequence of receptor PTK subfamily has three optional tyrosine residues (Y-749, Y-753 and Y-754) which can regulate Mer as autophosphorylation sites and interact with downstream signal molecules (Phosphatidylinositol-3-kinase (PI3K)/proteinkinase B (PKB) and mitogen-activated protein kinase (MAPK)). Activation of Mer kinase requires full phosphorylation of three tyrosine residues (see Ling, L. et al., "Identification of the major autophosphorylation sites of Nyk/Mer, an NCAM-related receptor tyrosine kinase," *Biol. Chem.*, 1996, 271(31):18355-18362).

Mer fails to occur in normal T and B lymphocytes and granulocytes, but abnormal expression of Mer in some malignant hematologic disease cell lines such as Jurkat, PEER, K562, and Raji is reported (see Graham, D. K., et al., "Cloning and mRNA expression analysis of a novel human proto-oncogene, c-mer," *Cell Growth Differ.*, 1994, 5(6): 647-657). This indicates that Mer relates to some malignant blood diseases. Mer TK also increases drug tolerance of lymphoblast. It has been found in studies on human Acute Lymphoblastic Leukemia (ALL) cell lines that expression of Mer TK can also increase drug tolerance of the drugs in treatment of ALL (see Linger, R. M., et al., "Mer receptor tyrosine kinase is a novel therapeutic target in pediatric B-cell acute lymphoblastic leukemia," *Blood*, 2009, 114 (13):2678-2687). In vivo experiments further proved that inhibition of Mer TK can reduce survival rate of leukemia cells and have a synergistic effect with other chemotherapies (see Lee-Sherick, A. B., et al., "Targeting pediatric acute lymphoblastic leukemia: novel therapies currently in development," *Br. J. Haematol.*, 2010, 151(4):295-311; Nguyen, K. et al., "Factors influencing survival after relapse from acute lymphoblastic leukemia: a children's oncology group study," *Leukemia*, 2008, 22(12):2142-2150; Scott, R. S. et al., "Phagocytosis and clearance of apoptotic cells is mediated by Mer," *Nature*, 2001, 411(6834):207-211.). Therefore, Mer tyrosine kinase inhibitors (Mer TKI) would be an effective drug in treatment of ALL.

FMS-like tyrosine kinase (FLT3) belongs to the Type III receptor PTK family. Genes of FLT3 are located in chromosome 13q12, with a total length of about 100 kb, contains 24 exons including 993 amino acids in coding. The relative molecular mass is 130,000 with its relative molecular mass is 160,000 in non-glycosylated form. FLT3 consists of an N-terminal extracellular domain including five immunoglobulin-like domains, one transmembrane domain, and one intracellular kinase domain (including a juxtamembrane domain and a kinase catalytic domain). The kinase catalytic domain of intracellular kinase domain consists of an N-terminal, a C-terminal containing an activation loop, and a flexible kinase insertion domain containing a binding site for ATP (see Liao, J. J., "Molecular recognition of protein kinase binding pockets for design of potent and selective kinase inhibitor," *J. Med. Chem.*, 2007, 50(3):409-424.).

The FLT3 mutation is the main cause of abnormal activation of FLT3. There are three main mutant forms: internal tandem duplication (ITD) of the juxtamembrane domain, TKD mutation, and juxtamembrane domain point mutation. Abnormal activation of FLT3 may cause ALL, acute myeloid leukemia (AML), and chronic myelogenous leukemia (CML) (see Hatzimichael, E. et al., "Profile of pacritinib and its potential in the treatment of hematologic disorder," *J. Blood Med.*, 2014, 5:143-152). Studies have shown that more than 70% of AML patients and ALL patients have high expression of FLT3 (see Smith, C. C., et al., "Validation of ITD mutations in FLT3 as a therapeutic target in human an acute myeloid leukaemia," *Nature*, 2012, 485(7397):260-263). Therefore, FLT3 can be used to treat leukemia as the target.

At present, many Mer PTK inhibitors and FLT3 PTK inhibitors have been reported. For example, the pyrrolopyrimidine compound MRX-2843, designed and developed by Wang et al., is a dual high-efficiency inhibitor of Mer PTK and FLT3 PTK, in addition to showing inhibition of other family members such as Axl/Tyro-3 of TAM PTK and other related PTKs. The structure of MRX-2843 has been disclosed in WO2013052417A1 and CN103958510 Å, and is depicted below:

MRX-2843

Formula I

Polymorphs of specific organic drug compounds have different physical properties such as solubility, hygroscopicity, and stability due to their unique three-dimensional structure. However, it is generally impossible to predict whether specific organic drug compounds will form different crystal forms, and it is less likely to predict the structure and properties of the crystal form itself. Exploring new crystal or polymorphic forms of pharmaceutically acceptable compounds provides an opportunity to improve the overall performance of pharmaceutical products while expanding the variety of materials available to formulation scientists. It is advantageous to expand the variety of the formulation by discovering new crystal forms of useful compounds.

SUMMARY OF THE INVENTION

The presently disclosed invention is directed to the compound of Formula I. (trans)-4-((2-cyclopropylethyl)amino)-5-(4-((4-methylpiperazin-1-yl)methyl)benzene-7H-pyrrolo[2,3-d]pyrimidin-7-yl)cyclohexanol trihydrochloride.

The invention also relates to multiple substantially pure crystal forms of the compound of Formula I, its hydrate, and/or its solvate.

In this invention, the compound, hydrates and/or solvate of the compound of Formula I, is present in one or more crystal forms.

In an embodiment, it is provided a crystal form of the compound of Formula I, its hydrate, and/or its solvate. In an embodiment, the X-ray powder diffraction pattern has a diffraction angle of 2θ with characteristic peaks of 5.7±0.2°, 17.7±0.2°, 19.7±0.2°, 22.7±0.2° and 23.2±0.2°. For convenience purpose, the crystal form characterized by this XRPD pattern is referred to as Crystal Form 1.

In another embodiment, the X-ray powder diffraction pattern of Crystal Form 1 has diffraction angle 2θ with characteristic peaks of 5.7±0.2°, 11.3±0.2°, 17.1±0.2°, 17.7±0.2°, 19.7±0.2°, 20.2±0.2°, 22.7±0.2° and 23.2±0.2°.

In another embodiment, the X-ray powder diffraction pattern of Crystal Form 1 has diffraction angle 2θ with characteristic peaks of 5.7±0.2°, 11.3±0.2°, 12.3±0.2°, 12.7±0.2°, 17.1±0.2°, 17.7±0.2°, 19.7±0.2°, 20.2±0.2°, 21.9±0.2°, 22.7±0.2°, 23.2±0.2° and 25.2±0.2°.

Figure 1:
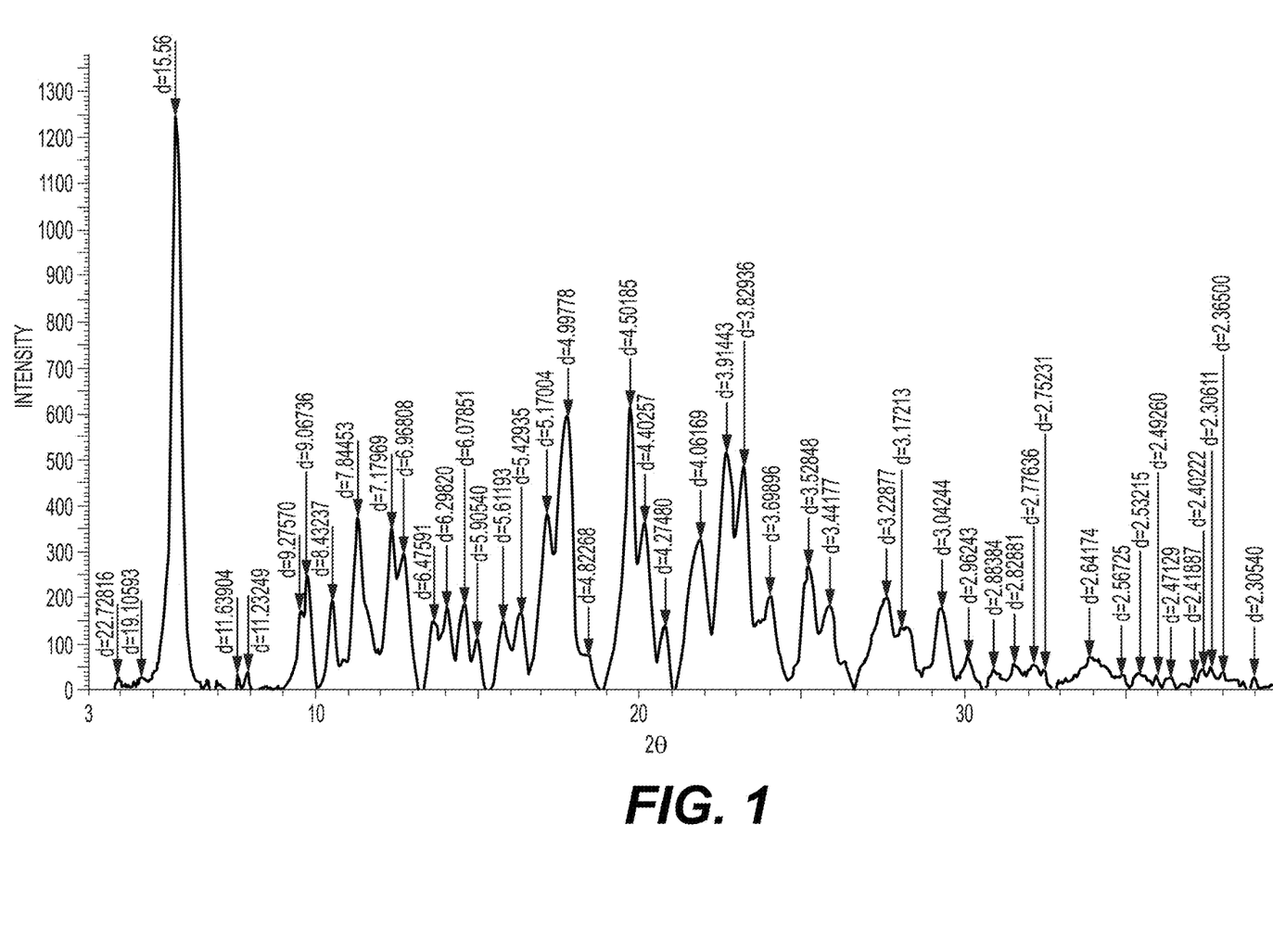
FIG. 1 shows the X-ray powder diffraction (XRPD) pattern of Crystal Form 1 of the compound of Formula I.

In another embodiment, the above Crystal Form 1 has an X-ray powder diffraction pattern as shown in FIG. 1.

The characteristic peaks of the X-ray powder diffraction spectrum of Crystal Form 1 where the relative intensity of the peaks is greater than 1000 is shown in Table 1.

TABLE 1

| SN | Intensity (I %) | 2θ (°) | Intensity | D Value |
|---|---|---|---|---|
| 1 | 100.0 | 5.7 ± 0.2 | 1255 | 15.5619 |
| 2 | 13.5 | 9.5 ± 0.2 | 170 | 9.2757 |
| 3 | 19.7 | 9.7 ± 0.2 | 247 | 9.0674 |
| 4 | 15.2 | 10.5 ± 0.2 | 191 | 8.4324 |
| 5 | 29.5 | 11.3 ± 0.2 | 371 | 7.8445 |
| 6 | 28.2 | 12.3 ± 0.2 | 354 | 7.1797 |
| 7 | 23.8 | 12.7 ± 0.2 | 298 | 6.9681 |
| 8 | 11.4 | 13.7 ± 0.2 | 144 | 6.4759 |
| 9 | 13.8 | 14.1 ± 0.2 | 173 | 6.2982 |
| 10 | 14.6 | 14.6 ± 0.2 | 183 | 6.0785 |
| 11 | 11.9 | 15.8 ± 0.2 | 149 | 5.6119 |
| 12 | 13.2 | 16.3 ± 0.2 | 165 | 5.4294 |
| 13 | 30.6 | 17.1 ± 0.2 | 384 | 5.1700 |
| 14 | 48.3 | 17.7 ± 0.2 | 607 | 4.9978 |
| 15 | 48.9 | 19.7 ± 0.2 | 613 | 4.5019 |
| 16 | 29.3 | 20.2 ± 0.2 | 367 | 4.4026 |
| 17 | 11.0 | 20.8 ± 0.2 | 138 | 4.2748 |

TABLE 1-continued

| SN | Intensity (I %) | 2θ (°) | Intensity | D Value |
|---|---|---|---|---|
| 18 | 26.2 | 21.9 ± 0.2 | 329 | 4.0617 |
| 19 | 41.2 | 22.7 ± 0.2 | 518 | 3.9144 |
| 20 | 38.8 | 23.2 ± 0.2 | 487 | 3.8294 |
| 21 | 16.2 | 24.0 ± 0.2 | 203 | 3.6990 |
| 22 | 21.0 | 25.2 ± 0.2 | 263 | 3.5285 |
| 23 | 14.6 | 25.9 ± 0.2 | 183 | 3.4418 |
| 24 | 15.8 | 27.6 ± 0.2 | 199 | 3.2288 |
| 25 | 10.6 | 28.1 ± 0.2 | 133 | 3.1721 |
| 26 | 14.5 | 29.3 ± 0.2 | 182 | 3.0424 |

In an embodiment, the purity of this crystal form is 85%. In another embodiment, the purity of this crystal form is 95%. In another embodiment, the purity of this crystal form is 99%. In another embodiment, the purity of this crystal form is ≥99.5%.

Figure 3:
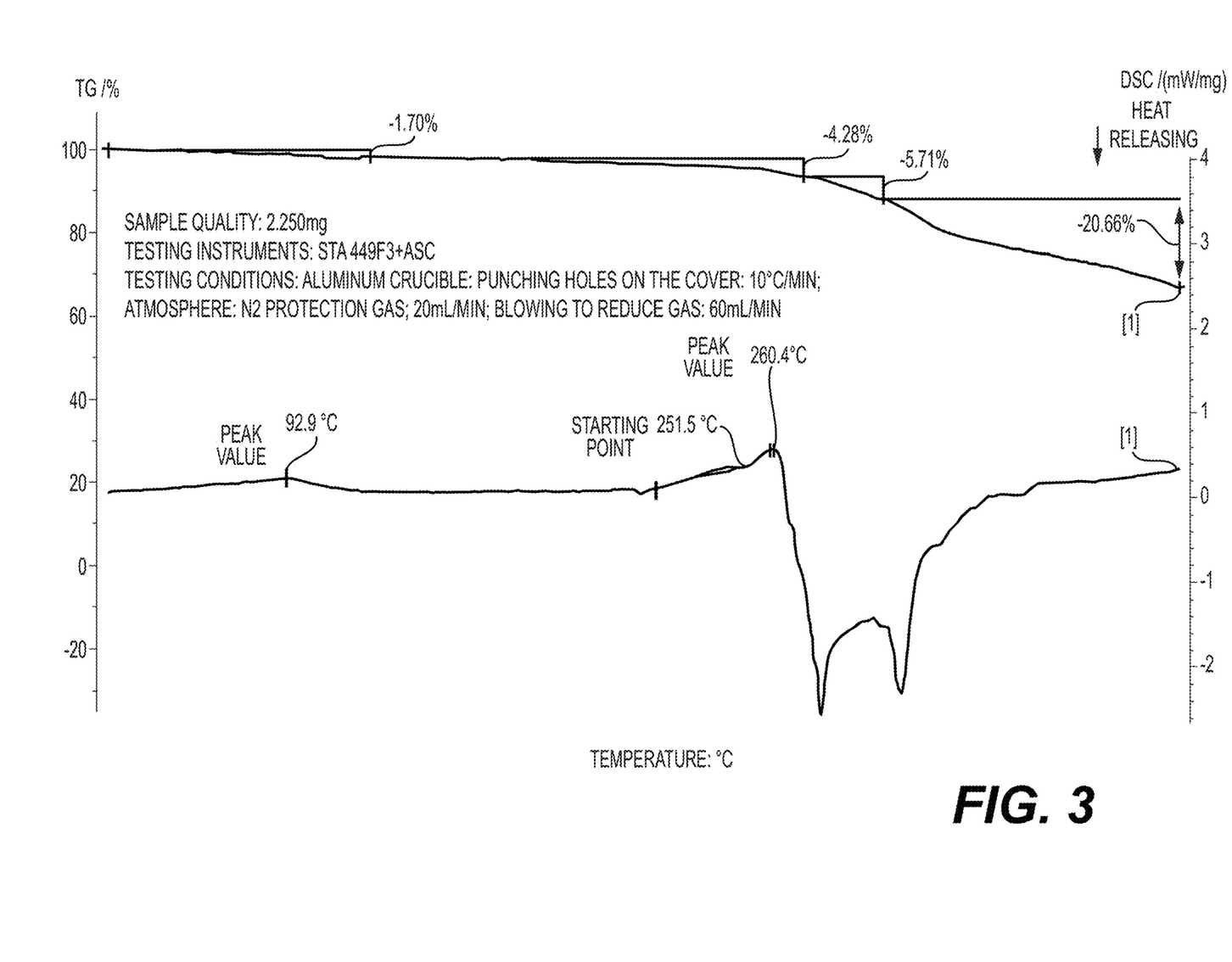
FIG. 3 shows the differential thermal-thermogravimetric analysis (DSC-TGA) pattern of Crystal Form 1 of the compound of Formula I.

Furthermore, Crystal Form 1 has the differential scanning calorimetry-thermogravimetric analysis (DSC-TGA) map as shown in FIG. 3.

In an alternate embodiment, the invention described herein further comprises the compound of Formula I in another crystal form of its hydrate and/or its solvate. In this embodiment, the X-ray powder diffraction spectrum of the crystal form has characteristic peaks with diffraction angles 2θ at 9.0±0.2°, 16.6±0.2°, 24.2±0.2°, 24.6±0.2°, and 24.8±0.2°. For convenience, the invention is referred to as Crystal Form 2.

In an embodiment, the X-ray powder diffraction spectrum of Crystal Form 2 has characteristic peaks with diffraction angles 2θ at 9.0±0.2°, 12.6±0.2°, 16.6±0.2°, 16.9±0.2°, 19.0±0.2°, 24.2±0.2°, 24.6±0.2°, and 24.8±0.2°.

Figure 2:
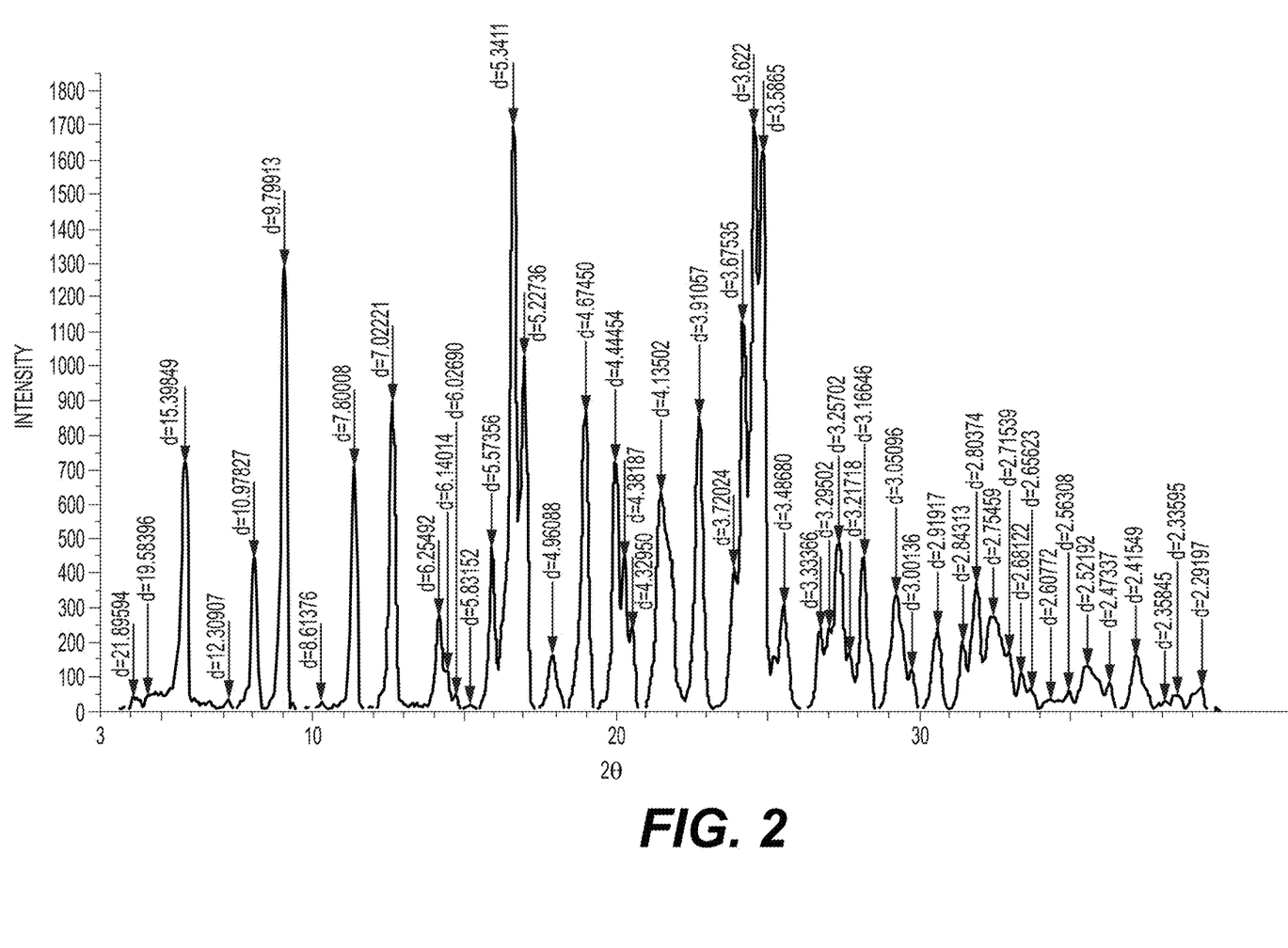
FIG. 2 shows the X-ray powder diffraction pattern of Crystal Form 2 of the compound of Formula I.

In another embodiment, the X-ray powder diffraction spectrum of Crystal Form 2 has characteristic peaks with diffraction angles 2θ at 5.7±0.2°, 9.0±0.2°, 11.3±0.2°, 12.6±0.2°, 16.6±0.2°, 16.9±0.2°, 19.0±0.2°, 20.0±0.2°, 22.7±0.2°, 24.2±0.2°, 24.6±0.2°, and 24.8±0.2° In another embodiment, Crystal Form 2 has the X-ray powder diffraction spectrum as shown in FIG. 2.

The characteristic peaks of the X-ray powder diffraction spectrum of Crystal Form 2 where the relative intensity of the peaks is greater than 10% is shown in Table 2.

TABLE 2

| SN | Intensity (I %) | 2θ (°) | Intensity | d Value |
|---|---|---|---|---|
| 1 | 42.9 | 5.7 ± 0.2 | 733 | 15.3985 |
| 2 | 25.8 | 8.0 ± 0.2 | 440 | 10.9783 |
| 3 | 75.9 | 9.0 ± 0.2 | 1296 | 9.7991 |
| 4 | 42.1 | 11.3 ± 0.2 | 719 | 7.8001 |
| 5 | 53.0 | 12.6 ± 0.2 | 905 | 7.0222 |
| 6 | 15.7 | 14.1 ± 0.2 | 268 | 6.2549 |
| 7 | 27.9 | 15.9 ± 0.2 | 477 | 5.5736 |
| 8 | 99.5 | 16.6 ± 0.2 | 1699 | 5.3412 |
| 9 | 60.1 | 16.9 ± 0.2 | 1026 | 5.2274 |
| 10 | 50.9 | 19.0 ± 0.2 | 869 | 4.6745 |
| 11 | 42.0 | 20.0 ± 0.2 | 718 | 4.4445 |
| 12 | 25.0 | 20.3 ± 0.2 | 427 | 4.3819 |
| 13 | 14.1 | 20.5 ± 0.2 | 241 | 4.3295 |
| 14 | 37.3 | 21.5 ± 0.2 | 636 | 4.1350 |
| 15 | 49.8 | 22.7 ± 0.2 | 851 | 3.9106 |
| 16 | 24.0 | 23.9 ± 0.2 | 409 | 3.7202 |
| 17 | 66.0 | 24.2 ± 0.2 | 1127 | 3.6754 |
| 18 | 100.0 | 24.6 ± 0.2 | 1708 | 3.6222 |
| 19 | 96.7 | 24.8 ± 0.2 | 1652 | 3.5865 |
| 20 | 17.7 | 25.5 ± 0.2 | 302 | 3.4868 |
| 21 | 13.9 | 26.7 ± 0.2 | 237 | 3.3337 |
| 22 | 14.0 | 27.0 ± 0.2 | 238 | 3.2958 |
| 23 | 28.5 | 27.4 ± 0.2 | 487 | 3.2570 |
| 24 | 25.9 | 28.2 ± 0.2 | 443 | 3.1665 |

TABLE 2-continued

| SN | Intensity (I %) | 2θ (°) | Intensity | d Value |
|---|---|---|---|---|
| 25 | 19.6 | 29.2 ± 0.2 | 334 | 3.0510 |
| 26 | 14.5 | 30.6 ± 0.2 | 239 | 2.9192 |
| 27 | 12.0 | 31.4 ± 0.2 | 204 | 2.8431 |
| 28 | 21.5 | 31.9 ± 0.2 | 368 | 2.8037 |
| 29 | 15.9 | 32.5 ± 0.2 | 272 | 2.7546 |

The above crystal forms may be characterized using only a summary of the main peaks. These main peaks are reproducible within a margin of error of 0.2.

As used herein, the phrase "having an X-ray powder diffraction pattern as shown in FIG. 1" or "having an X-ray powder diffraction pattern as shown in FIG. 2" means that main peaks of the X-ray powder diffraction pattern are shown in FIG. 1 or FIG. 2, where the main peaks mean those peaks with relative intensity value greater than 10%, and preferably greater than 30%, compared with the highest peak in FIG. 1 or FIG. 2 (relative intensity is specified as 100%).

In an embodiment, the purity of Crystal Form 2 is ≥85%. In another embodiment, the purity of Crystal Form 2 is ≥95%. In another embodiment, the purity of Crystal Form 2 is ≥99%. In another embodiment, the purity of Crystal Form 2 is ≥99.5%.

Figure 4:
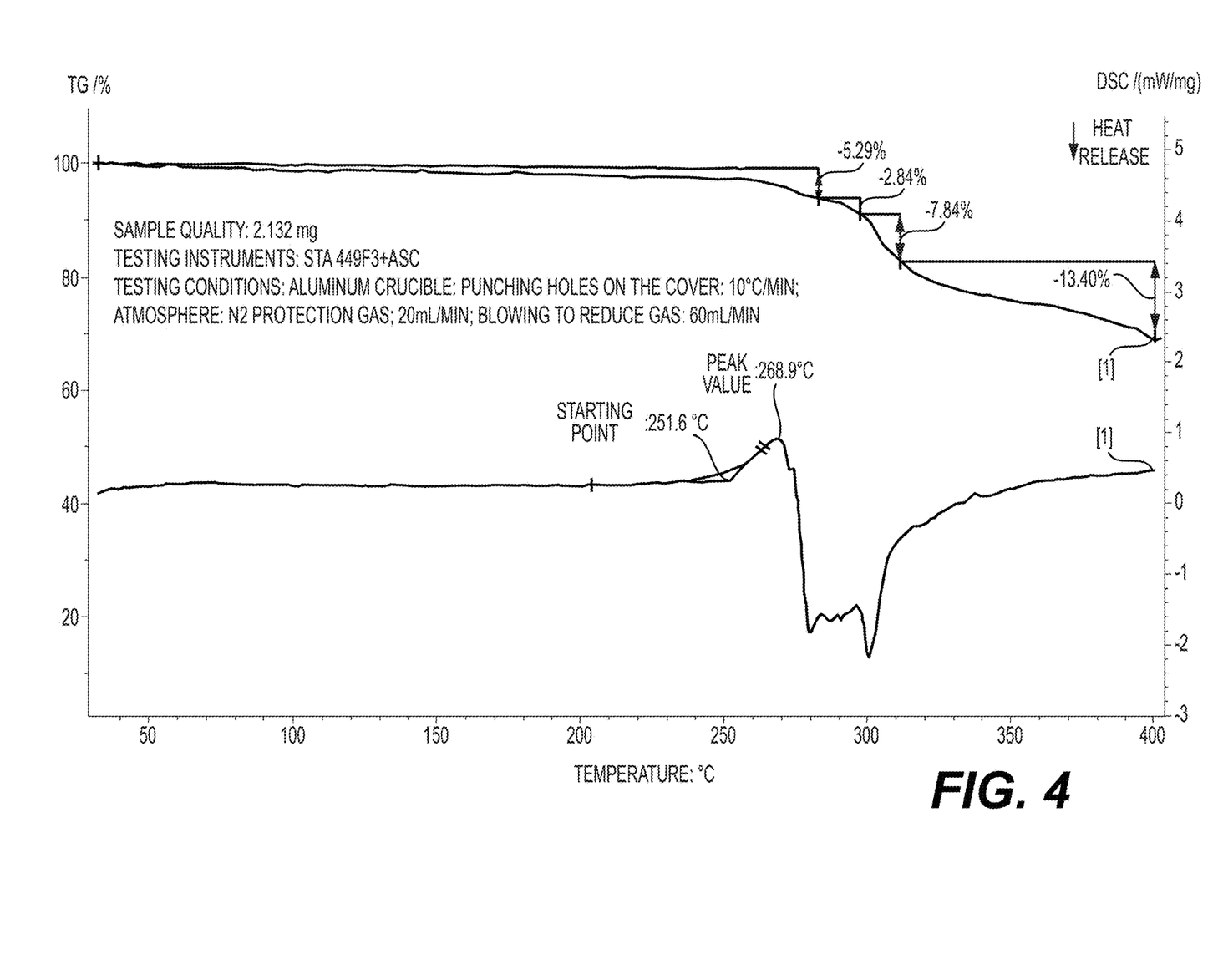
FIG. 4 shows the DSC-TGA pattern of Crystal Form 2 of the compound of Formula I.

Furthermore, Crystal Form 2 has the differential thermal-thermogravimetric analysis (DSC-TGA) map as shown in FIG. 4.

In an embodiment, the invention also provides a pharmaceutical composition comprising a therapeutically effective amount of Crystal Form 1 and/or Crystal Form 2 as described above.

The invention also provides embodiments of the pharmaceutical composition as described above:

In an embodiment, the described pharmaceutical composition contains a therapeutically effective amount of Crystal Form 1 or Crystal Form 2, as well as pharmaceutically acceptable excipients, adjuvants or carriers.

In another embodiment, the described pharmaceutical composition contains a therapeutically effective amount of Crystal Form 1 and Crystal Form 2 presented by this invention, as well as the pharmaceutically acceptable excipients, adjuvants or carriers.

In another embodiment, the pharmaceutical composition contains a therapeutically effective amount of Crystal Form 1 or Crystal Form 2 and at least one other therapeutic agent.

In another embodiment, the pharmaceutical composition contains a therapeutically effective amount of Crystal Form 1 and Crystal Form 2 and at least one other therapeutic agent.

In an embodiment, the pharmaceutical composition is an oral preparation.

In an embodiment, the pharmaceutical composition is a tablet or capsule.

In an embodiment, the pharmaceutical composition comprises from 5 to 150 mg of Crystal Form 1 and/or Crystal Form 2, formulated with a total amount of from about 50 mg to 800 mg with at least one excipient, adjuvant, and/or carrier.

In an embodiment, the excipient, adjuvant, and/or carrier in the pharmaceutical composition are microcrystalline cellulose, pregelatinized starch, cellulose lactose, crospovidone, micronized silica gel, magnesium stearate, and/or hydroxypropyl cellulose.

In an embodiment, the pharmaceutical composition contains 0.01% by weight to 99% by weight of Crystal Form 1 or Crystal Form 2. In other embodiments, the pharmaceutical composition contains 0.01% by weight to 70% by weight, 1% by weight to 70% by weight, 1% by weight to 50% by weight, 1% by weight to 30% by weight, or 10% by weight to 30% by weight of Crystal Form 1 or Crystal Form 2.

In an embodiment, the described pharmaceutical composition contains 0.01% by weight to 99% by weight of Crystal Form 1 and Crystal Form 2 of the invention. In other embodiments, the pharmaceutical composition contains 0.01% by weight to 70% by weight, 1% by weight to 70% by weight, 1% by weight to 50% by weight, 1% by weight to 30% by weight, or 10% by weight to 30% by weight of Crystal Form 1 and Crystal Form 2.

The invention also provides the usage of the described Crystal Form 1 and/or Crystal Form 2 in the production of pharmaceuticals for treating patients' diseases, symptoms or conditions, wherein the disease, symptoms or conditions are mediated by Mer and/or FLT3.

The invention also provides embodiments for the use of Crystal Form 1 and/or Crystal Form 2 in the treatment of diseases, symptoms, or conditions.

In an embodiment, the described diseases, symptoms, or conditions are cancers and/or proliferative diseases.

In an embodiment, the described diseases, symptoms, or conditions are myeloid leukemia, lymphoblastic leukemia, melanoma, breast cancer, lung cancer, colon cancer, liver cancer, stomach cancer, kidney cancer, ovarian cancer, uterine cancer, and/or brain cancer. In a further embodiment, the described diseases, symptoms or conditions are myeloid leukemia and/or lymphoblastic leukemia.

In an embodiment, the invention also provides methods of treating patients' diseases, symptoms or conditions by administering to the patient the compound of Formula I having Crystal Form 1 and/or Crystal Form 2 as provided herein.

The invention further provides embodiments of the above-mentioned methods of treating patients' diseases, symptoms or conditions by using the described Crystal Form 1 and/or Crystal Form 2:

In an embodiment, the diseases, symptoms or conditions are mediated by Mer and/or FLT3.

In an embodiment, the described diseases, symptoms or conditions are cancer and/or proliferative disease.

In an embodiment, the described diseases, symptoms or conditions are myeloid leukemia, lymphoblastic leukemia, melanoma, breast cancer, lung cancer, colon cancer, liver cancer, stomach cancer, kidney cancer, ovarian cancer, uterine cancer, and/or brain cancer. In a further embodiment, the described diseases, symptoms or conditions are myeloid leukemia and/or lymphoblastic leukemia.

The invention further provides a process for the preparation of the compound of Formula I:

In an embodiment, the method for the preparation of the compound of Formula I comprises the following steps:
a) contacting compound M-1 with compound M-2 to obtain the compound M-3;
b) contacting compound M-3 with compound M-4 in the presence of a palladium catalyst to obtain compound M-5; and
c) performing a crystallization method to obtain the compound of Formula I.

The invention further provides intermediates in the preparation of the compound of Formula I. Such intermediates include M-3, pictured below:

This invention further provides methods for preparing Crystal Form 1 and Crystal Form 2 of the compound, its hydrate and/or its solvate.

In one embodiment, the preparation methods of Crystal Form 1 are as follows:

M-5, HOAc, activated carbon, and Si-Thiol are added to a reaction flask, stirred at room temperature for 14 hours (except palladium) and then filtered with 50 g of diatomaceous earth. The filtrate is transferred to a reaction flask to cool down, and 3N HCl CPME solution is added at 0° C.±5° C. At first, ½ of the total volume of the 3N HCl CPME is added, and the remaining ½ is dropped into the mixture until there is solid precipitation. After the addition is completed, MTBE is added to the mixture. The whole dropping process is temperature controlled at 0° C.±5° C. After adding MTBE dropwise, thermal insulation is used to maintain the temperature at 0° C.±5° C., the mixture is stirred for 1 hour and crystallized. The resultant solid is filtered, the filter cake is rinsed with MTBE, and the mixture is vacuum dried at 45° C. Then 500 mL of ethanol is added at room temperature, the mixture is filtered and dried at 45° C. to obtain Crystal Form 1.

In an alternate method, M-5 and 7 L acetic acid are added to a reaction kettle where the mixture is stirred and dissolved. After dissolution, Si-Thiol and activated carbon are added. The mixture is stirred for 16 hours while the whole process is temperature controlled at 15-20° C. To this mixture is added 500 g of diatomaceous earth, the mixture is filtered, and 2.1 L of acetic acid used to rinse the filter cake. The filtrate is transferred to the reaction kettle and 3N HCl CPME solution is added dropwise at a temperature of 15-20° C. After the addition is complete, methyl tert-butyl ether is added and the mixture is stirred for 1 hour. The crystalized product is then filtered. The filter cake is rinsed with 1 L of methyl tert-butyl ether and the filter cake is dried under vacuum for 15 hours with gradient heating from 20° C. to 45° C. The sample obtained is crushed and added to the reaction kettle. 15 L of ethyl acetate is added at room temperature, then the mixture is stirred, beaten and filtered. The filter cake is dried under vacuum at 45° C. The above sample is added to the reaction kettle, 15 L of ethyl acetate is added and stirred at room temperature, while twice beating and filtering. The filter cake is dried under vacuum at 45° C. for 3 hours, then heated to 80° C. and dried under vacuum for 15.5 hours to obtain a yellow solid, which is Crystal Form 1.

In an embodiment, the preparation of Crystal Form 1 comprises the steps of:
a) mixing M-5, HOAc, activated carbon, and Si-Thiol in a reaction flask;
b) blending the mixture at room temperature;
c) filtering the mixture from step b;
d) adding 3N HCl CPME to the filtrate from step c at a temperature of 0° C.±5° C.; and
e) filtering the mixture from step d to obtain Crystal Form 1.

In another embodiment, the preparation of Crystal Form 1 comprises the steps of.
a) mixing M-5 and acetic acid into a reaction vessel until dissolved;
b) adding Si-Thiol and activated carbon;
c) stirring the resulting mixture for a period of time while the temperature is controlled at 15-20° C.;
d) filtering the mixture from step c;
e) adding 3N HCL CPME to the filtrate from step d;
f) adding methyl tert-butyl ether to the mixture from step e;
g) filtering the mixture from step f to obtain a solid;
h) adding ethyl acetate to the solid obtained in step g; and
i) filtering the resulting mixture to obtain Crystal Form 1.

Crystal Form 2 may be prepared as follows:

Crystal Form 1 (about 80 g) is beaten with 500 mL ethanol at room temperature for 2.5 hours, filtered, and the filter cake is dried at 45° C. to obtain a solid sample of 75.01 g. This sample is used to make a 7.5% aqueous solution of 1500 mL. The mixture is kept at 50° C., stirred, and beaten for 16.5 hours. The mixture is cooled to room temperature for filtration, and the filter cake is dried at 45° C. to obtain Crystal Form 2.

In an alternate method, an 80 L jacketed reactor with bottom of glass is equipped with two single-channel chart recorders and a thermal control unit. Nitrogen gas is applied to the reactor for 15 mins. A 7.5% v/v aqueous ethanol solution is prepared in a clean glass vial. A transfer line equipped with an in-line filter (10 micron) and the compound of Formula I is added in an 80 L reactor with a 7.5% v/v aqueous ethanol solution (12.5 L). The temperature is adjusted to 50±5° C. and the reactor contents are stirred for 17 hours. The batch temperature is raised to 20±5° C. over 140 mins and then stirred at 20±5° C. for 1 h. The batch material is filtered and washed with a pre-filtered aqueous ethanol solution (2.1 L). The filter cake is kept in nitrogen gas for 1 h and then is sampled for HPLC analysis. The filter cake is dried in vacuum at 45±5° C. to a constant weight over about 87 hours, and then the residual EtOH is sampled. The batch material is dried for another 24 hours to obtain 1967 g of Crystal Form 2.

In an embodiment, the method for preparing Crystal Form 2 comprises the steps of:
a) mixing Crystal Form 1 in ethanol;
b) filtering the mixture to obtain a solid sample;
c) adding the solid sample to an aqueous ethanol solution;
d) stirring the mixture while beating; and
e) filtering the resulting solid, to obtain Crystal Form 2.

In another embodiment, the method for preparing Crystal Form 2 comprises the steps of:
a) mixing a compound of Formula I with a 7.5% v/v aqueous ethanol solution;
b) heating the mixture for a period of time;
c) cooling the mixture to approximately room temperature; and
d) filtering the resulting mixture to to obtain Crystal Form 2.

All crystal forms of the invention are substantially pure. As used herein, the term "substantially pure" means that at least 85 wt %, preferably at least 95 wt %, more preferably at least 99 wt %, and most preferably at least 99.5 wt % of the compound of Formula I is present in the crystal forms of this invention, especially in Crystal Form 1 and/or Crystal Form 2.

As used herein, the term "adding methanol/acetone" or the like involved in the preparation method of Crystal Form 1 or Crystal Form 2 means that methanol is first added, and then acetone is added in the preparation method. Similarly, "ethanol/water" means that ethanol is first added, and then water is added; and "trifluoroethanol/ethyl acetate" means that trifluoroethanol is first added, and then ethyl acetate is added. Similarly, "solvent 1/solvent 2" means that solvent is first added, and then solvent 2 is added; and "solvent 2/solvent 1" means that solvent 2 is first added, and then solvent 1 is added.

Definitions

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. The subject matter should be understood by reference to appropriate portions of the entire specification of this patent, any or all drawings and each claim.

The term "patient" or "subject" refers to an animal, such as a mammal, including but not limited to primates, such as humans, cows, sheep, goats, horses, dogs, cats, rabbits, rats, mice, etc. In an embodiment of this invention, the "patient" or "subject" refers to a human being.

The term "about" means that the values described may include ±20% of the specific value, such as ±10%, such as ±5%, ±1%, ±0.5%, or ±0.1% according to the invention, to implement the technical proposal of this invention.

As used herein, the term "crystal form" is not only to mean "crystal type" or "crystal structure", but the "crystal form" is more understood as a "substance with a specific crystal structure" or a "crystal with a specific crystal type."

As used herein, the "crystal form" may be characterized by its representative X-ray diffraction pattern. Those technicians in the field can understand that the experimental error depends on the conditions of instruments, preparation of the sample, and purity of the sample. It is understood in the field that the X-ray diffraction pattern usually varies with the conditions of instruments. In addition, the experimental error of the peak angle is usually 5% or less, and the error of these angles should also be taken into account, allowing an error of ±0.2° in general. Due to the influence of experimental factors such as the height of the sample, an overall shift of the peak angle occurs, and a certain offset is usually allowed. Thus, a crystal form that has the same or similar characteristic peaks is a within the scope of this invention.

As used herein, the term "room temperature" refers to a conventional room temperature, generally 10 to 30° C.

As used herein, the term "pharmaceutically acceptable" means that it is present in the form or amount which does not adversely affect the subject to be administered.

As used herein, the term "therapeutically effective amount" refers to an amount with which one compound is sufficient to treat a disease, illness or symptom of a disease. "Therapeutically effective amount" can vary with the compound, disease, illness, and/or symptom of the disease or illness, the severity of the symptoms of the disease, condition, and/or disease or illness, the age of the patient being treated, and/or body weight of the patient being treated. In any specific condition, a suitable amount may be apparent to those technicians in the field or may be determined by routine experimentation. In the case of combination therapy, "therapeutically effective amount" means the total amount to effectively treat a disease, illness or symptom of a subject.

All dosage forms of the pharmaceutical compositions in this invention can be prepared by conventional methods in the pharmaceutical field. For example, the active ingredient may be mixed with one or more excipients and then prepared into the desired dosage form.

As used herein, the term "pharmaceutically acceptable carrier" means a conventional pharmaceutical carrier suitable for the desired pharmaceutical preparation, for example, a diluent and an excipient such as water, various organic solvents and so on; a filler such as starch, pregelatinized starch, sucrose, mannitol, lactose, spray-dried lactose, microcrystalline cellulose, silicified microcrystalline cellulose, and cellulose lactose; a binder such as cellulose derivative, alginate, gelatin, hydroxypropyl cellulose and polyvinylpyrrolidone (PVP); a wetting agent such as glycerin; a disintegrant such as agar, calcium carbonate, crospovidone, croscarmellose sodium, sodium carboxymethyl starch and sodium hydrogen carbonate; an absorption enhancer such as a quaternary ammonium compound; a surfactant such as cetyl alcohol, sodium lauryl sulfate and tween; an absorption carrier such as kaolin and bentonite; a lubricant such as talc, stearic acid, calcium stearate, magnesium stearate, sodium stearyl fumarate, micro powder silica gel and polyethylene glycol. It is also possible to add other pharmaceutically acceptable excipients to the pharmaceutical composition such as a dispersing agent, stabilizer, thickener, complexing agent, buffer, penetration enhancer, polymer, fragrance, sweetener, or dye. It is preferred to use excipients suitable for the desired dosage form and desired mode of administration.

As used herein, the term "disease", "illness" or "symptom" refers to any disease, discomfort, illness, symptom or indication.

As used herein, the term "additional therapeutic agent" refers to an agent which elicits therapeutic response in a disease, illness, or symptom to be treated. Non-limiting examples of additional therapeutic agents include a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, and agent for treating diabetes, and an agent for treating immunodeficiency disorders.

EXAMPLES

The invention is further illustrated by the following embodiments, which are not intended to limit the scope of this invention. Unless otherwise specified, in specific embodiments of the invention, the techniques or methods are routine technologies or methods in the field.

Unless otherwise stated, in the following embodiments and effect embodiments, information on testing instruments and testing method parameters to be used are as follows:
(1) X-ray powder diffractometer (XRD), Bruker D8 Advance diffractometer; Technical Specifications: Kα irradiation (40 Kv, 40 mA) with a copper target wavelength at 1.54 Å, θ-2θ goniometer, Mo monochromator, Lynxeye probe; standard materials: $Al_2O_3$; acquisition software: Diffrac Plus XRD Commander; analytical software: MDI Jade 6; Method parameters: testing angle, 3-40° 2θ/3-30° 2θ (thermal table XRD); step size, 0.02° 2θ; speed, 0.15 s/step; testing sample quantity >2 mg.

(2) Synchronous thermal analyzer (DSC-TGA), STA 449F3; sample tray: aluminum crucible; testing sample dosage: 0.5-5 mg; shielding gas: nitrogen; gas flow rate: 20 mL/min; purge gas: 60 mL/min; testing method: heating rate 10° C./min, balanced at 30° C. and then raises the temperature up to 400° C. For details, refer to GB/T 19267.12-2008, Section 12, physical and chemical examination of trace evidence of forensic technology: thermal analysis.

(3) Nuclear magnetic resonance spectrometer (NMR), Agilent DD2 600 MHz; type of testing: Proton NMR spectra and carbon spectrum; testing method: General Principles under JY/T 007-1996 for superconducting pulse Fourier transformation of nuclear magnetic resonance spectrum.

Abbreviations:
API: Active Pharmaceutical Ingredients
$^{13}$C-NMR: $^{13}$C nuclear magnetic resonance;
CPME: cyclopentyl methyl ether;
DIPEA: N, N-diisopropylethylamine;
DSC-TGA: differential thermal-thermogravimetric analysis;
EtOH: Ethanol;
h or hours: hour;
$^{1}$H-NMR: $^{1}$H nuclear magnetic resonance;
HOAc: Acetic acid;
HPLC: High performance liquid chromatography;
IPA: Isopropanol;
LC-MS: Liquid chromatography-mass spectrometry;
Min or mins: minute;
MTBE: Methyl tert-butyl ether;
Pd(Ph$_3$P)$_4$: Tetrakis (triphenylphosphine) palladium;
PO: Peros;
RH: Relative humidity;
XRD: X-ray powder diffraction.

Implementation Case 1: Synthesis of the Compound of Formula I

Synthesis of Compound M-3

An 80 L jacketed reactor with glass bottom is equipped with two single-channel chart recorders and a thermal control unit. Nitrogen gas is applied to the reactor for 75 mins, and then isopropanol, M-1, M-2 and diisopropyl ethyl amine is added in the reactor. The batch temperature is adjusted to 97±5° C. and the reactor contents are stirred for 85 hours. The batch material is sampled for HPLC analysis. The batch temperature is adjusted to 20±5° C. and the batch material is stirred overnight. Pure water is added in the reactor over about 30 mins. When the batch temperature is at 20±5° C., methyl tert-butyl ether is added to the reactor and the contents are stirred for 25 mins. The layers are separated and the aqueous phase is extracted with MTBE. The organic layer is washed with pure water and then distilled to a volume of 5.5 L under vacuum while maintaining the batch temperature ≤40° C. After adjusting the jacket temperature to 20±5° C., acetonitrile is added to the reactor. The batch temperature is adjusted to 0±5° C. and the reactor contents are stirred overnight. The filtrate is used as the auxiliary filtering batch and the filter cake is washed with acetonitrile. The filter cake is kept under nitrogen gas for 4 hours and then sampled for HPLC analysis. The filter cake is dried in a vacuum oven at 40±5° C. until constant weight is about 21 hours.

LC-MS[M+H$^+$]: 379.1.

Synthesis of Compound M-5 (MRX-2843 Free Base)

An 80 L jacketed reactor with glass bottom is equipped with two single-channel chart recorders and a thermal control unit. The reactor is kept under nitrogen flow overnight. M-3, M-4, and potassium carbonate are added to the reactor with a mixture of ethyl alcohol and water and nitrogen gas is bubbled into the mixture for 1 hour.

Tetra(triphenylphosphine)palladium is added, and the batch temperature is adjusted to 40° C. The reactor contents are stirred at 40±5° C. for 2 hours. The batch temperature is raised to 58±5° C. and the mixture is stirred for 18 hours. Then batch sampling is adopted for HPLC analysis and no M-3 is detected. The batch material is distilled to a volume of 10 L under vacuum while maintaining the batch temperature ≤60° C. The batch temperature is adjusted to 58±5° C. and kept at this temperature while adding ethyl acetate to the reactor. The mixture is stirred for 29 mins. The layers are separated and the organic layer is washed with pure water at 58±5° C. The batch temperature is adjusted to 20±5° C., M-5 seed crystal is added to the reactor and the contents are stirred overnight. The batch material is distilled to a volume of 8 L under vacuum while maintaining the jacket temperature ≤40° C. After adjusting the jacket temperature to 20±5° C., acetonitrile is added to the reactor. The mixture is cooled to 10±5° C. and stirred for about 1.5 hours. The filtrate is used as the auxiliary filtering batch and the filter cake is washed with ethyl acetate. The filter cake is kept under nitrogen gas for 1 h and dried to a constant weight in a vacuum oven at 30±5° C.

LC-MS[M+H$^+$]: 489.3.

Synthesis of the Compound of Formula I

A 22 L jacketed reactor with a glass bottom is equipped with two single-channel chart recorders and a thermal control unit. Nitrogen gas is applied to the reactor for 1 h. M-5 and glacial acetic acid are added in the reactor and stirred until dissolution is discovered. The batch temperature is adjusted to 25±5° C. Activated carbon and Si-thiol are added to the reactor and the contents are stirred at 25±5° C. for 19 hours. The mixture is passed through a Celite® filter pad and any loose Celite® is pulpified in glacial acetic acid and an in-line filter. The filter cake is washed with glacial acetic acid and the filtrate is transferred to an 80-liter jacketed reactor with a glass bottom equipped with two single-channel chart recorders and a thermal control unit via an inline filter. The batch temperature is adjusted to 5±5° C. and kept at this temperature while 3N HCl is added in CPME. The batch temperature is adjusted to 0±5° C., and MTBE is added via an in-line filter at this temperature over 40 mins. The reactor contents are stirred at 0±5° C. for 1 h, filtered, and washed with pre-filtered MTBE. The filter cake is dried under nitrogen gas for 14.5 hours and dried to a constant weight in a vacuum oven at 45±5° C. This results in 27,279 g of crude product. The crude product and ethyl alcohol are added to an 80 L reactor and the contents are stirred at 20±5° C. for 18.5 hours. The batch material is filtered, and the filter cake is washed with pre-filtered ethyl alcohol. The filter cake is kept under nitrogen gas for 3.5 hours and dried to a constant weight under vacuum at 45±5° C.

Figure 5:
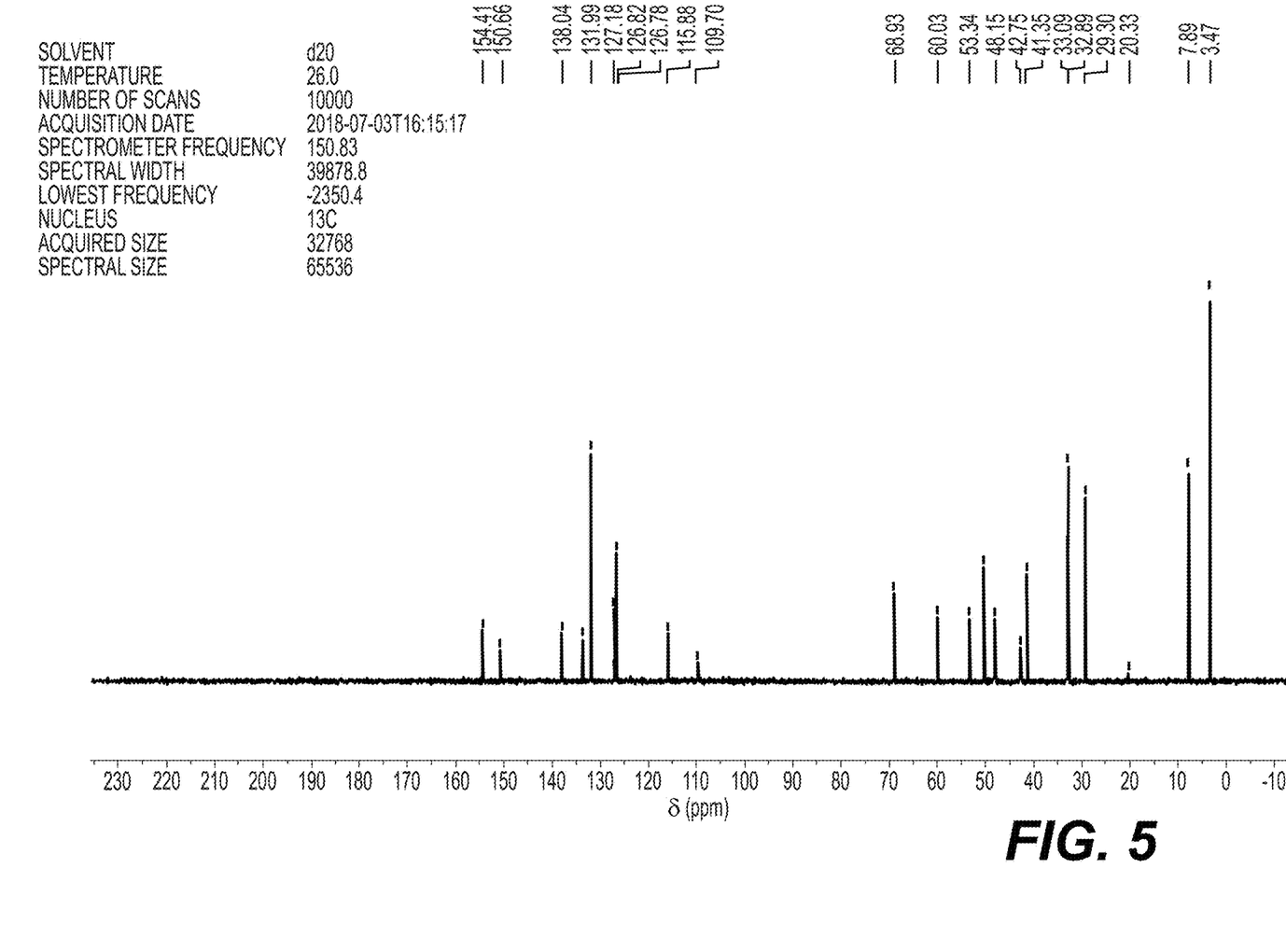
FIG. 5 shows the $^{13}$C-NMR pattern of Crystal Form 1 of the compound of Formula I. The compound of Formula I and the $^{13}$C-NMR pattern of Crystal Form 2 sample are consistent with those in FIG. 5.
Figure 6:
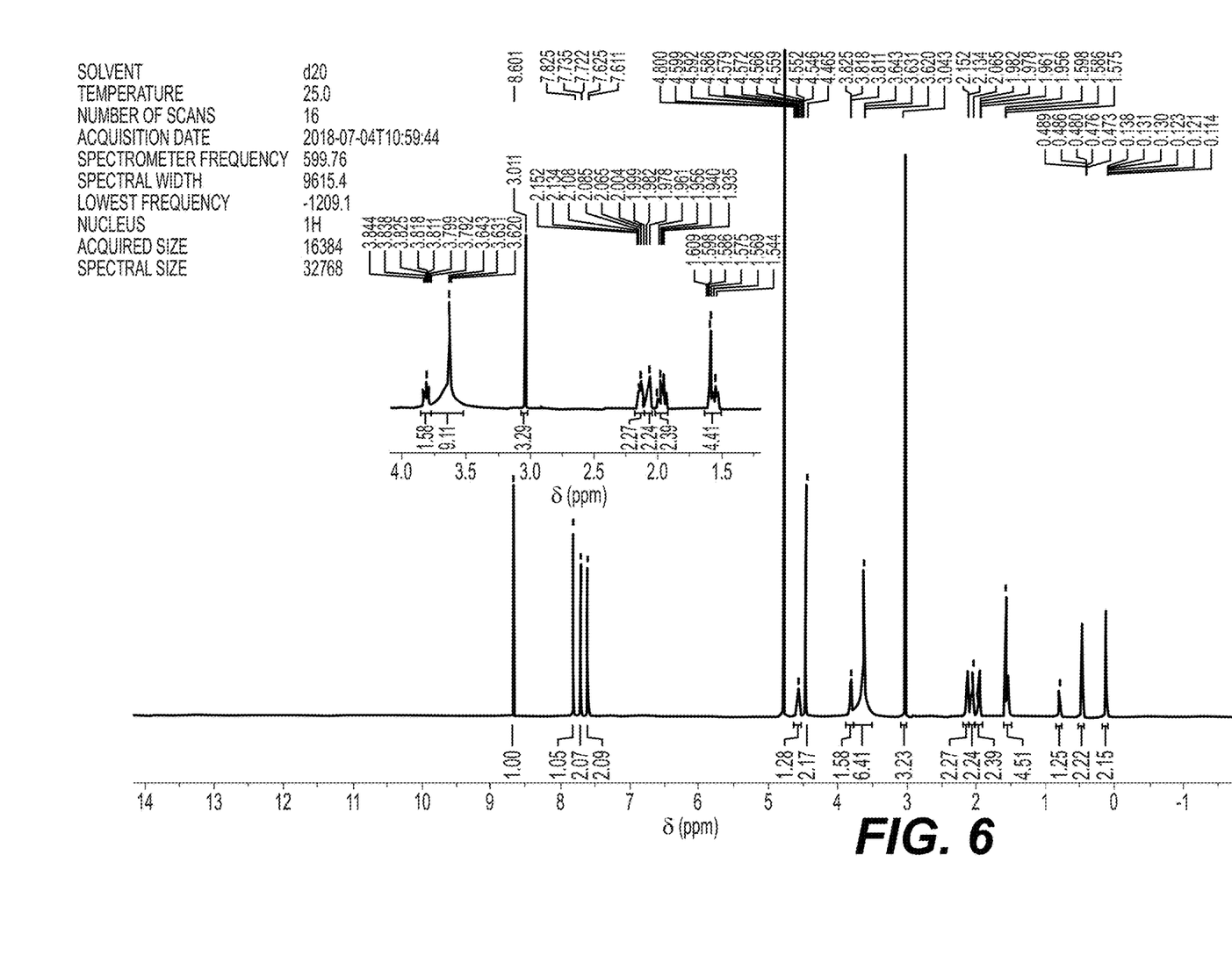
FIG. 6 shows the $^{1}$H-NMR pattern of the Crystal Form 2 of the compound of Formula I. The $^{1}$H-NMR pattern of the compound of Formula I and the sample of the Crystal Form 1 are consistent with those in FIG. 6.

$^1$H NMR and $^{13}$C NMR patterns are consistent with those shown in FIGS. 5 and 6.

LC-MS[M+H$^+$]597.3.

Embodiment 2: Preparation Method of Crystal Form 1

Method 1

M-5, HOAc, activated carbon, and Si-Thiol are added to a reaction flask, stirred at room temperature for 14 hours (except palladium) and then filtered with 50[[ ]]g of diatomaceous earth. The filtrate is transferred to a reaction flask to cool down, and 3N HCl CPME solution is added at 0° C.±5° C. Firstly, adding ½ of the total volume, continuing to add the remaining ½ until there is solid precipitation. After the addition is completed, MTBE is added to the system and the whole dropping process temperature is controlled at 0° C.±5° C. After adding MTBE, thermal insulation is adopted at 0° C.±5° C. The mixture is stirred and crystallized for 1 hour with filtering and the filter cake is rinsed with MTBE. After the filter cake is dried under vacuum at 45° C., 500 mL of ethanol is beaten at room temperature, the mixture filtered, and the filter cake dried at 45° C. to obtain Crystal Form 1. $^1$H NMR and $^{13}$C NMR patterns are consistent with those shown in FIGS. 5 and 6.

Method 2

M-5 and 7 L acetic acid are added to the reaction kettle to stir and dissolve. After dissolution, Si-Thiol and activated carbon are added and the mixture stirred for 16 hours, while the whole process is temperature controlled at 15-20° C. 500 g of diatomaceous earth is added for filter aid, 2.1 L acetic acid is used for rinsing the filter cake, and the filtrate is transferred to the reaction kettle. Then 3N HCl CPME solution is added at a temperature of 15-20° C. After the addition is completed, methyl tert-butyl ether is added and the mixture is stirred, crystallized for 1 h, and filtered. The filter cake is rinsed with 1 L methyl tert-butyl ether and the filter cake is dried under vacuum for 15 hours with gradient heating at 20 to 45° C. The sample obtained is crushed and added to the reaction kettle. 15 L of ethyl acetate is added at room temperature. The mixture is stirred, beaten and filtered, and the filter cake is then dried under vacuum at 45° C. The above sample is added to the reaction kettle, 15 L of ethyl acetate is added and stirred at room temperature, with twice beating and filtering. The filter cake is dried under vacuum at 45° C. for 3 hours, then heated up to 80° C. and dried under vacuum for 15.5 hours to obtain a yellow solid, i.e. Crystal Form 1. $^1$H NMR and $^{13}$C NMR patterns are consistent with those shown in FIGS. 5 and 6.

Embodiment 3: Preparation Method of Crystal Form 2

Method 1

Crystal Form 1 (about 80 g) is beaten with 500 mL ethanol at room temperature for 2.5 hours, filtered, and the filter cake is dried at 45° C. to obtain a solid sample of 75.01 g. The resultant sample is added in a 7.5% aqueous solution of 1500 mL, kept at 50° C., stirred, and beaten for 16.5 hours. The mixture is cooled down to room temperature for filtration and the filter cake is dried at 45° C. to obtain Crystal Form 2. $^1$H NMR and $^{13}$C NMR patterns are consistent with those shown in FIGS. 5 and 6.

Method 2

An 80 L jacketed reactor with a glass bottom is equipped with two single-channel chart recorders and a thermal control unit. Nitrogen gas is applied to the reactor for 15 mins. A 7.5% v/v aqueous ethanol solution is prepared in a clean glass vial. A transfer line equipped with an in-line filter (10 micron) and the compound of Formula I is added in the 80 L reactor with a 7.5% v/v aqueous ethanol solution (12.5 L). The batch temperature is adjusted to 50±5° C. and the reactor contents are stirred for 17 hours. The batch temperature is raised to 20±5° C. over 140 mins and then stirred at 20±5° C. for 1 hour. The batch material is filtered and washed with a pre-filtered aqueous ethanol solution (2.1 L). The filter cake is kept under nitrogen gas for 1 h and then is sampled for HPLC analysis. The filter cake is dried in vacuum at 45±5° C. to a constant weight for about 87 hours and then the residual EtOH is sampled. The batch material is dried for another 24 hours to obtain 1967 g of Crystal Form 2. $^1$H NMR and $^{13}$C NMR patterns are consistent with those shown in FIGS. 5 and 6.

Embodiment 4: Determination of Crystal Form Stability

Crystal form 1 is stored at 25° C./60% RH and 40° C./75% RH for 1, 3 and 6 months. Under these conditions, the crystal form remains unchanged.

Crystal form 2 is stored at 5° C. for 18 and 24 months, and the crystal form remains unchanged. It is stored at 25° C./60% RH for 1, 3, 6, 9, 12, 18 and 24 months, and the crystal form remained unchanged. It is stored at 40° C./75% RH for 1, 3 and 6 months, the crystal form is unchanged.

Embodiment 5: Determination of Saturated Solubility

An appropriate amount of a sample of the compound is supersaturated in water at a pH of 1-8 and shaken at 37° C. for 4 hours with a shaker. The compound is sampled, centrifuged, then the supernatant is diluted and tested by HPLC. Calculations are compared to an external standard.

The saturated solubility of the compound of Crystal Form 1 and Crystal Form 2 of the compound of Formula I and MRX-2843 free base at 37° C. in different pH values are shown in Table 3.

TABLE 3

| pH Value | Crystal Form 1 (mg/mL) | Crystal Form 2 (mg/mL) | MRX-2843 free base (mg/mL) |
| --- | --- | --- | --- |
| 1.0 | 586.76 | 535.05 | 301.086 |
| 2.0 | 489.60 | 531.72 | 3.110 |
| 3.0 | 522.25 | 512.80 | 1.516 |
| 4.5 | 513.40 | 527.84 | 2.034 |
| 6.0 | 460.64 | 546.95 | 0.018 |
| 6.8 | 554.17 | 557.34 | 0.008 |
| 7.4 | 494.83 | 516.01 | 0.007 |
| 8.0 | 562.59 | 479.26 | 0.008 |

Embodiment Example 6. Capsule Formulation and Preparation

The capsule formulation is shown in Table 4.

TABLE 4

| Ingredients | 10 mg Intensity Capsule (g/batch) | 40 mg Intensity Capsule (g/batch) | 100 mg Intensity Capsule (g/batch) |
| --- | --- | --- | --- |
| Batch (Number of capsules) | 4000 | 750 | 300 |
| Crystal Form 1$^a$ | 48.9600 | 36.7200 | 36.7200 |
| Microcrystalline cellulose PH-102 | 146.8800 | 18.3600 | 18.3600 |
| Pregelatinized starch 150 | 48.9600 | 18.3600 | 18.3600 |
| Total amount (mixed powder) | 244.8000 | 73.4400 | 73.4400 |
| Gelatin capsule | QS (Sufficient) | QS (Sufficient) | QS (Sufficient) |

$^a$The unit content of the active pharmaceutical ingredient (API) of Crystal Form 1 is adjusted according to the theoretical salinity. The actual dosage is based on the API content.

The manufacturing process of the capsule is as follows:
1) API crushing/screening
   The drug substance is crushed and sieved once with a 20-mesh screen.
2) Mix
   Microcrystalline cellulose PH-102, pregelatinized starch 1500 and sieved drug substance are added in the V-type mixer for 20 min.
3) 40 mg size capsule filling
   Take 30% mixture and fill it with No. 4 white conical gelatin capsule.
4) 100 mg size capsule filling
   Take 30% mixture and fill it with No. 1 white conical gelatin capsule.
5) 10 mg size capsule filling
   Take 50% proportion of the mixture of microcrystalline cellulose PH102 and 10% proportion of the mixture of pregelatinized starch 1500 and the remaining material to mix for 20 min. Fill it with 5th white conical gelatin capsules.
6) Final packaging
   The capsule is filled into a 100 ml high-density polyethylene bottle, and a desiccant is added, and a foil-type induction sealing gasket and a child safety cover are used for sealing.

Embodiment 7: Formulation and Preparation of Tablets

Tablet formula is shown in Table 5:

TABLE 5

| Ingredients | 10 mg intensity tablet (g/batch) | 40 mg intensity tablet (g/batch) | 100 mg intensity tablet (g/batch) |
| --- | --- | --- | --- |
| Batch (Number of pieces) | 3000 | 3000 | 3000 |
| Crystal Form 1$^a$ | 36.7200 | 146.8800 | 367.2000 |
| Cellulose lactose | 90.2400 | 360.9600 | 902.4000 |
| Pregelatinized starch | 90.2400 | 360.9600 | 902.4000 |
| Cross-linked povidone | 9.6000 | 38.4000 | 96.0000 |
| Hydroxypropyl cellulose | 9.6000 | 38.4000 | 96.0000 |
| Micro-silica gel | 1.2000 | 4.8000 | 12.0000 |
| Magnesium stearate | 2.4000 | 9.6000 | 24.0000 |
| Total amount (core) | 240.0000 | 960.0000 | 2,400.0000 |
| Purified water $^b$ | QS (Sufficient) | QS (Sufficient) | QS (Sufficient) |
| Opad @II Orange | 7.2000 | 28.8000 | 72.0000 |
| Total amount (coated tablets) | 247.2000 | 988.8000 | 2,472.0000 |

$^a$The unit content of the active pharmaceutical ingredient (API) Crystal Form 1 is adjusted according to the theoretical salinity. The actual dosage is based on the API content.
$^b$Removal during processing.

The manufacturing process of the tablet is as follows:
1) API crushing/screening
   Crystal form 1 is crushed and sieved once with an 80-mesh screen.
2) Premix
   The cellulose lactose is added to the hopper mixer and then the drug substance is crushed and sieved, crospovidone and hydroxypropyl cellulose are added, and finally the pregelatinized starch is added and mixed for 10 minutes.
3) Material handling
   The mixed material is passed over the swinging granulator (24-mesh sieve) twice.

4) Middle mixing

Transfer the material to the hopper mixer, pass the micro-powder silica gel through a 40-mesh sieve and add it to the mixer for 30 minutes.

5) Total mixing

Magnesium stearate is sieved through a 40-mesh sieve and mixed with the mixture for 5 minutes.

6) Tableting

The final mixed product is pressed into an oval (100 mg) or round core (10 mg, 40 mg), and the weight, thickness and hardness of the tablet are inspected in the process.

7) Coating

The core is coated and dried with a high-efficiency coating pan, and the tablet temperature is controlled at 38° C.-42° C. The loose tablets are packed in double-layer zipper bags, sealed and placed in aluminum-plastic composite film bags. 25 g of desiccant is placed between the interlayers, and the labels are stored in the packaging process after marking.

8) Final packaging

The tablets are packaged in a double aluminum packaging machine and marked with code spray. The packaging material is cold stamping solid pharmaceutical composite hard tablet of polyamide/aluminum/polyvinyl chloride and medicinal aluminum foil.

Embodiment 8: Pharmacokinetic Data

Nine male beagle dogs are divided into three groups, three in each group. They are each respectively administrated a 5 mg/kg oral capsule (PO) of Crystal Form 1, Crystal Form 2 and free base of the compound of Formula I (the dose is calculated according to the dose of the free base). Blood is collected from the jugular vein before administration and after administration for 15 minutes, 30 minutes, 1 hour, 2 hours, 4 hours, 6 hours, 8 hours, 10 hours, and 24 hours, and the plasma is separated and stored in a refrigerator at −80° C. LC-MS is subsequently used for analysis.

The experimental data is shown in Table 6:

TABLE 6

| Compound | Administration | Dosage (mg/kg) | $T_{max}$ (hours) | $C_{max}$ (ng/mL) | $AUC_{last}$ (h * ng/mL) | $AUC_{Inf}$ (h * ng/mL) |
|---|---|---|---|---|---|---|
| Free base of the compound of Formula I | PO | 5 | 3.33 | 285 | 1,169 | 1,318 |
| Crystal Form 1 | PO | 5 | 2.67 | 133 | 1,397 | 1,617 |
| Crystal Form 2 | PO | 5 | 2.00 | 125 | 1,323 | 1,530 |

From the above results, it is suggested that Crystal Form 1 and Crystal Form 2 of the compound of Formula I are better absorbed in the body than the free alkali of the compound of Formula I.

Although presently disclosed subject matter has been fully described through the implementation of various methods and reference figures, it is worth noting that changes and modifications will be apparent to those technicians in the field. Such changes and modifications shall be within the scope of the appended claims of the invention.

That which is claimed:

1. A crystal form of the compound of Formula I, its hydrate and/or a solvate thereof,

Formula I

3HCl wherein the crystal form is characterized by an X-ray powder diffraction pattern comprising peaks at 5.7±0.2°, 17.7±0.2°, 19.7±0.2°, 22.7±0.2°, and 23.2±0.2° degrees 2θ.

2. The crystal form of claim 1, wherein the crystal form is characterized by the X-ray powder diffraction pattern shown in FIG. 1.

3. A crystal form of the compound of Formula I, its hydrate and/or a solvate thereof, Formula I 3HCl wherein the crystal form is characterized by an X-ray powder diffraction pattern comprising peaks at 9.0±0.2°, 16.6±0.2°, 24.2±0.2°, 24.6±0.2°, and 24.8±0.2° degrees 2θ.

4. The crystal form of claim 3, wherein the crystal form is characterized by the X-ray powder diffraction pattern shown in FIG. 2.

5. The crystal form of claim 1, where the purity of the crystal form is ≥85%.

6. The crystal form of claim 1, wherein the crystal form is characterized by the DSC-TGA pattern shown in FIG. 3.

7. The crystal form of claim 3, wherein the crystal form is characterized by the DSC-TGA pattern shown in FIG. 4.

8. A pharmaceutical composition comprising the crystal form of claim 1, and a pharmaceutically acceptable excipient, adjuvant, and/or carrier.

9. The pharmaceutical composition of claim 8, further comprising at least one additional therapeutic agent.

10. The pharmaceutical composition of claim 8, wherein the pharmaceutical composition is in the form of a tablet or capsule.

11. A method of treating cancer in a patient in need thereof, wherein the method comprises administering to the patient the pharmaceutical composition of claim 8, and wherein the cancer is selected from the group consisting of myeloid leukemia, lymphoblastic leukemia, melanoma, breast cancer, lung cancer, colon cancer, liver cancer, stomach cancer, kidney cancer, ovarian cancer, uterine cancer and brain cancer.

12. A method for the preparation of a compound of Formula I,

Formula I

3HCl the method comprising:
  a) contacting compound M-1 with compound M-2 to obtain the compound M-3;
  b) contacting compound M-3 with compound M-4 in the presence of a palladium catalyst to obtain compound M-5; and
  c) performing a crystallization method to obtain the compound of Formula I.

13. A method for preparing the crystal form of claim 1, the method comprising:
  a) mixing M-5, HOAc, activated carbon, and Si-Thiol in a reaction flask;
  b) blending the mixture at room temperature;
  c) filtering the mixture from step b;
  d) adding 3N HCl CPME to the filtrate from step c at a temperature of 0° C.±5° C.; and
  e) filtering the mixture from step d to obtain the crystal form of claim 1.

14. A method for preparing the crystal form of claim 1, the method comprising:
  a) mixing M-5 and acetic acid into a reaction vessel until dissolved;
  b) adding Si-Thiol and activated carbon;
  c) stirring the resulting mixture for a period of time while the temperature is controlled at 15-20° C.;
  d) filtering the mixture from step c;
  e) adding 3N HCL CPME to the filtrate from step d;
  f) adding methyl tert-butyl ether to the mixture from step e;
  g) filtering the mixture from step f to obtain a solid;
  h) adding ethyl acetate to the solid obtained in step g; and
  i) filtering the resulting mixture to obtain the crystal form of claim 1.

15. A method of preparing the crystal form of claim 3, the method comprising:
  a) mixing the crystal form of claim 1 in ethanol;
  b) filtering the mixture to obtain a solid sample;
  c) adding the solid sample to an aqueous ethanol solution;
  d) stirring the mixture while beating; and
  e) filtering the resulting solid, to obtain the crystal form from claim 3.

16. A method of preparing the crystal form of claim 3, the method comprising:
  a) mixing a compound of Formula I with a 7.5% v/v aqueous ethanol solution;
  b) heating the mixture for a period of time;
  c) cooling the mixture to approximately room temperature; and
  d) filtering the resulting mixture to to obtain the crystal form of claim 3.

* * * * *